(12) United States Patent
Buchanan

(10) Patent No.: US 6,722,882 B2
(45) Date of Patent: Apr. 20, 2004

(54) DENTAL INSTRUMENTS FOR USE WITH ULTRASONIC HANDPIECES

(75) Inventor: L. Stephen Buchanan, Santa Barbara, CA (US)

(73) Assignee: Earth City Technologies, Inc., Fenton, MO (US)

( * ) Notice: Subject to any disclaimer, the term of this patent is extended or adjusted under 35 U.S.C. 154(b) by 0 days.

(21) Appl. No.: 10/367,176

(22) Filed: Feb. 14, 2003

(65) Prior Publication Data

US 2003/0157458 A1 Aug. 21, 2003

Related U.S. Application Data

(60) Provisional application No. 60/357,617, filed on Feb. 15, 2002.

(51) Int. Cl.$^7$ ................................................. A61C 1/07
(52) U.S. Cl. ........................................ 433/119; 433/166
(58) Field of Search ............................... 433/118, 119, 433/166, 165

(56) References Cited

U.S. PATENT DOCUMENTS

| | | | | |
|---|---|---|---|---|
| 2,990,616 A | * | 7/1961 | Balamuth et al. | 433/119 |
| 4,283,175 A | * | 8/1981 | Nash | 433/165 |
| 4,731,019 A | * | 3/1988 | Martin | 433/166 |
| 5,100,321 A | * | 3/1992 | Coss et al. | 433/118 |
| 5,971,758 A | * | 10/1999 | Hugo et al. | 433/118 |
| 2003/0096213 A1 | * | 5/2003 | Hickok et al. | 433/119 |

* cited by examiner

Primary Examiner—Cary E. O'Connor
(74) Attorney, Agent, or Firm—Polster, Lieder, Woodruff & Lucchesi, LC

(57) ABSTRACT

An ultrasonic dental instrument or tip is disclosed for performing endodontic procedures. The instrument has a hub adapted to be operatively coupled to the output of an ultrasonic handpiece and a shank portion extending from the hub. A first portion of the shank extends in a generally axial direction from the hub and tip portion extends from the first portion. The shank has a bend therein between the first portion and the tip portion ranging between about 90° and about 140°. One embodiment of the tip has an enlarged, bulbous free end, with the latter having an end face cross sectional area larger than the cross sectional area of the tip portion proximate the enlarged free end. The enlarged free end has an abrasive coating thereon so that upon activation of the instrument by the transducer, the tip portion and the enlarged free end vibrates in a plane including the shank and tip portions. Other embodiments of the tip have radiused ends so that they do not leave troughs or scratches in the canal which obfuscate canals.

8 Claims, 2 Drawing Sheets

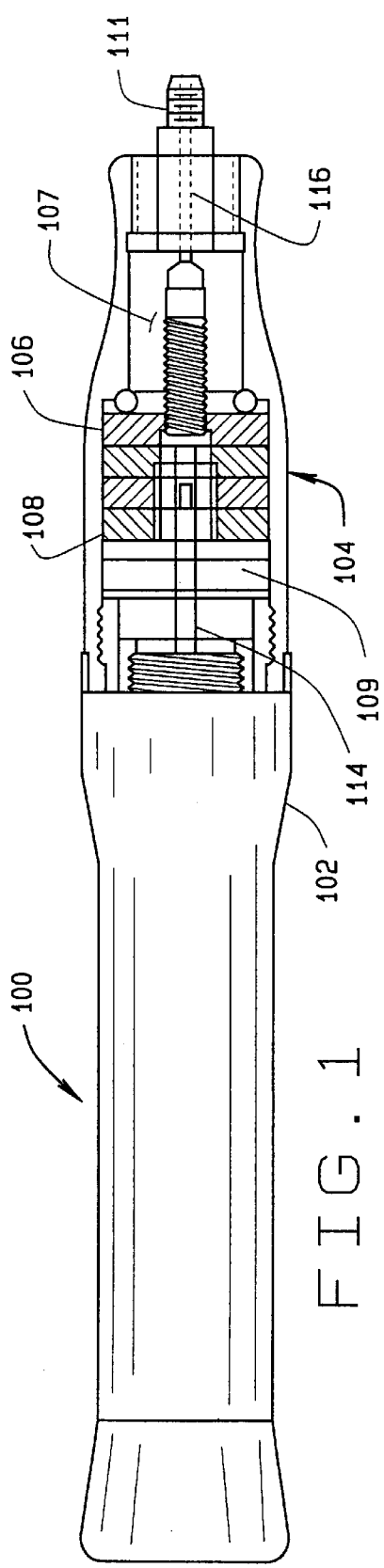
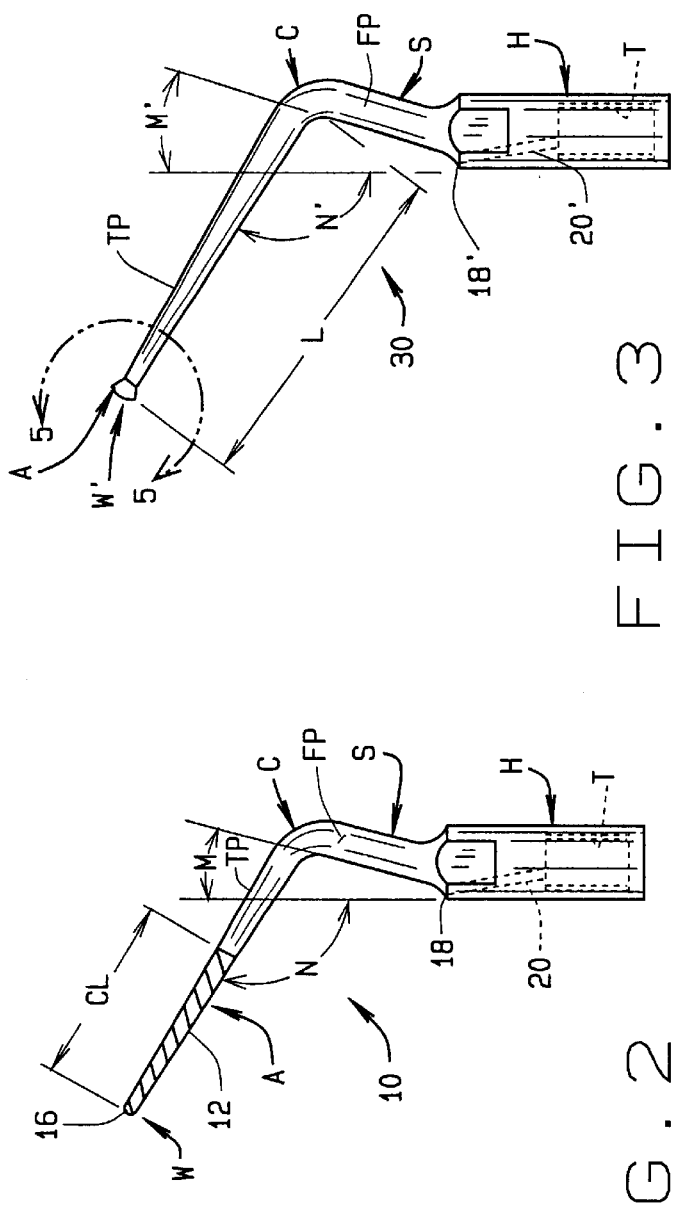
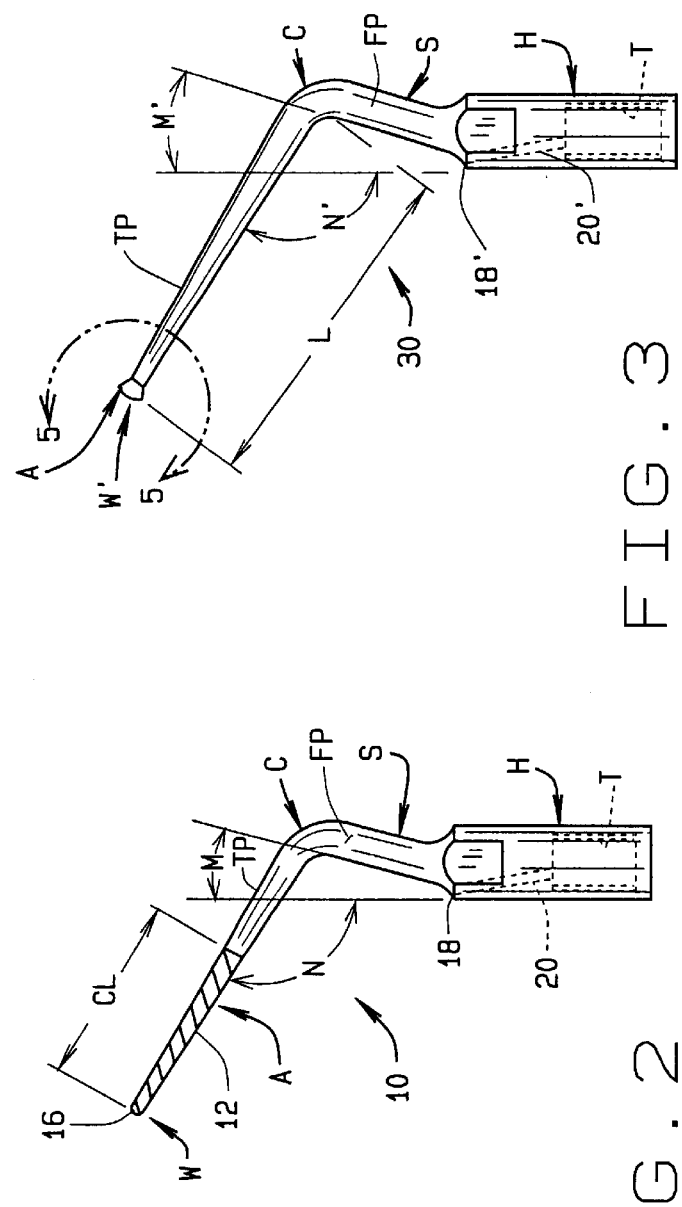

DENTAL INSTRUMENTS FOR USE WITH ULTRASONIC HANDPIECES

CROSS REFERENCE TO RELATED APPLICATION

This application claims priority to provisional application Ser. No. 60/357,617, filed Feb. 15, 2002.

BACKGROUND OF THE INVENTION

This invention relates to ultrasonic dental tools or instruments, and, more particularly, to ultrasonic instruments or tips which when installed on an ultrasonic handpiece and which when energized with ultrasonic energy resonate such that the when the vibrating tip is brought into working contact with tooth material, the tip will abrade the tooth material in contact with the working end of the tip such that the tooth material can be removed in a controlled fashion. Even more specifically, such ultrasonic tips are useful in carrying out a variety of dental procedures, such as tooth cleaning, and are useful in preparing the canal of a tooth during root canal and endodontic procedures. Such ultrasonic dental tips are known, as shown in U.S. Pat. Nos. 5,094,617, and 5,868,570, and International Publication No. WO 00/74586.

In performing root canals, it is important for the clinician to have visibility of the canal with the instrument in operation, particularly when performing root canals deep within root structure. Prior art ultrasonic instruments have, in the past, provided improved visibility over rotary driven instruments (e.g., burs) because the high speed rotary handpiece head driving the bur is eliminated which opens up the field of view into the canal and of the instrument. However, there is still a need for better visibility while using ultrasonic tips, particularly when the cutting tip of the instrument is deep in the canal.

In performing root canals in maxillary molars, it is important to search for, to locate, and to treat MB2 canals. Such MB2 canals are present a large percentage of the time and they often have separate portals of exit. Locating and entering such MB2 canals with conventional instruments is difficult and time consuming. When such canals are located, it is difficult to maneuver conventional instruments into such canals during treatment. Ineffective geometries of prior art ultrasonic tips have made the location of such MB canals difficult because such prior art tips had sharp tips which created clefts and ditches in the pulp chamber floor which, in many instances, had the appearance of MB canal fins when such canal was not present. If a smooth trough can be created, particularly when viewed under magnification, a distinct line may be seen to extend between the MB1 orifice in a palatal direction to the MB2 canal. However, conventional ultrasonic tips are not effective in creating such smooth troughs.

It is also important to be able to smooth pulp chamber floors without cutting past the floor. In molars it is necessary to plane through the lighter colored calcific dentin to gain access to the darker colored pulp chamber floor dentin. With conventional ultrasonic tips, ditching often occurs which obscures the pulp chamber floor anatomy.

While the above-noted prior art tips have worked well for their intended purposes, there has been a need for an ultrasonic tip that is especially adapted for cutting of dentin and enamel and which maximizes the clinician's field of view of the operating site while using the tip to prepare for root canal procedures. There has also been a need for an ultrasonic tip that allows the practitioner to horizontally smooth pulp chambers when performing a root canal and to safely plane attached pulp stones in the canal without cutting past the stone. Still further, there has been a need for a tip that is extremely active when rendered resonant at ultrasonic frequencies for cutting apically into calcified canals and for digging around posts that may have become embedded in the canal.

SUMMARY OF THE INVENTION

Among the several objects and features of the present invention may be noted the provision of a series of ultrasonic tips for use with an ultrasonic dental handpiece which when activated may be efficiently used to eliminate clefts and ditches in the pulp chamber floor, for cutting and refinement of line angles, for smoothing the walls of the canal, and for cutting MB troughs when performing root canal procedures;

The provision of such tips which permits the practitioner to readily smooth pulp chamber floors and to safely plane attached pulp stones without cutting past them;

The provision of such tips which are highly active when energized and which enable the practitioner to readily cut apically into calcified canals and around posts;

The provision of such tips that provide micro-abrasion cutting efficiency when energized;

The provision of such tips which have geometries that aid visibility of the practitioner during use in the tooth;

The provision of a tip which smoothes the cutting action and minimizes ledging and perforations;

The provision of such tips which facilitates the location of and access to MB2 canals in molars;

The provision of such tips which improves the field of view of the operating site and which optimizes the ability of the practitioner to use loupes and microscopes during root canal surgery, particularly when the tip is deep in the canal; and The provision of such tips which are shaped so that they are comfortable for the practitioner to use, which are shaped so that the tip is in the proper position to perform its intended function as the clinician holds the handpiece in the conventional manner, which is readily activated when the handpiece is energized, which has a long service life, which readily cuts through dental materials, and which is easily maneuvered and controllable in the operating site.

A dental instrument of the present invention is for use with an ultrasonic dental handpiece for performing endodontic procedures. The handpiece has an ultrasonic transducer therein and an output stud or chuck which is operatively coupled to the transducer such that when the transducer is rendered resonant, the output chuck is vibrated in axial direction. The instrument further has a hub adapted to be operatively coupled (e.g., threaded) to the output chuck. A first shank portion extends from the hub in a generally axial direction and tip portion of the shank extends from the first portion. The shank has a bend therein (sometimes referred to as a contra angle) between the first portion and the tip portion ranging between about 90° and about 140°. The tip portion has a generally bulbous (enlarged) free end with the latter having a cross sectional area (or diameter) of about one-and-one-half times to about twice (or even larger) the cross sectional area of the tip portion proximate the bulbous free end.

Further, the bulbous free end has an abrasive coating thereon (preferably on its end face) so that upon activation of the instrument by the transducer, the tip portion and the bulbous free end vibrate in a plane.

Stated differently, the dental instrument of the present invention has a hub adapted to be operatively coupled to the output chuck and a shank portion extending from the hub. The shank has a first portion that extends in a generally axial direction from the hub and tip portion extends from the first portion. The shank has a bend therein between the first portion and the tip portion ranging between about 90° and about 140°. The tip portion has a free distal end with the latter having a radius ranging between about 0.25 mm. and about 1.00 mm. such that when the tip is rendered resonant by the transducer and is brought into operating engagement with a tooth, the radiused distal end will remove dental material from the tooth substantially without scratching the tooth thereby facilitating visual identification of the canal in the tooth.

Other objects and features of the present invention will be in part apparent and in part pointed out hereinafter.

BRIEF DESCRIPTION OF THE DRAWINGS

FIG. 1 is a view with parts shown broken away and in cross section illustrating an ultrasonic dental handpiece having an ultrasonic transducer therein for transmitting ultrasonic energy from the transducer to the output end of the handpiece to which an instrument, as shown in FIGS. 2–7, may be operatively attached and rendered resonant;

FIG. 2 is an elevational view of a first embodiment of an instrument or tip of the present invention having a hub for threadable connection to the output of the handpiece and having a shank with a contra angle therein leading to a working end of the tip coated with an abrasive coating, such as diamond grit, and having an enlarged rounded cutting surface on its distal end;

FIG. 3 is an elevational view of another embodiment of the tip of the present invention having a bulbous end with a radiused outer surface constituting the operating surface of the tip with micro-abrasive coating applied thereto for enabling horizontal planing of pulp chamber floors and the like;

FIG. 4 is an elevational view of another tip of the present invention having a shank with a contra angle and having a micro-abrasive coating applied to the distal end portion thereof, and having the provision of a surgical irrigation fluid port located proximate the distal end portion for irrigating the operating site with water, gas, or other surgical irrigation fluid for flushing the site of debris and the like;

Corresponding reference characters indicate corresponding parts throughout the several views of the drawings.

DESCRIPTION OF PREFERRED EMBODIMENTS

Figure 4:
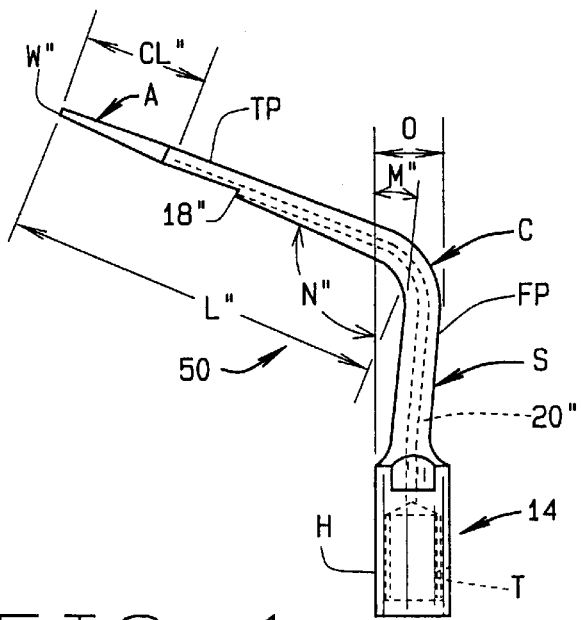

Referring now to the drawings, in FIG. 1 there is illustrated an ultrasonic handpiece, as generally indicated at 100. The handpiece has a body 102 which is configured so as to conveniently held by a clinician using the handpiece. Within the handpiece, an ultrasonic transducer 104 is provided. Typically, such a transducer comprises a stack of piezoelectric wafers 106, 108 which vibrate upon being energized by oscillating electrical power supplied by a remotely located power supply (not shown) connected to the handpiece by a cable (not shown) in the well known manner. The piezoelectric wafers 106, 108 are firmly clamped between a front mass 107 and a back mass 109. The front mass 107 has a threaded stud 111 extending longitudinally from the handpiece. As is conventional, the instruments or tips 10, 30, 50 and 70 of the present invention (as described in detail below) each have a threaded recess within the hub at its proximal end having internal threads T which threadably receive the external threads on stud or chuck 111 so as to permit a an instrument or tip of the present invention to be secured to the handpiece and to be removed therefrom. Such a threaded connection between the transducer 104 and the instrument or tool effectively transmits vibrations from the transducer to the tool. While chuck 111 is shown to threadably engage the ultrasonic instruments of this invention, it will be understood that within the broader aspects of this invention, any suitable connection between the handpiece and the instrument may be used that efficiently transmits ultrasonic energy from the handpiece to the instrument. For example, in place of a threaded connection, a variety of friction and mechanical interlocking arrangements may be used such as are typically to chuck a tool to drive. Another example of a connection suitable for attaching the instrument to the handpiece may be a bayonet locking arrangement or the like.

Upon energization of the transducer 104 by the power supply (not shown) at its predetermined frequency (e.g., about 40,000 Hz.), the transducer will cause the threaded stud 111 to vibrate in longitudinal or axial direction substantially at the frequency of the transducer (e.g., about 40,000 Hz.). The amplitude of these vibrations will vary in proportion to the power supplied to the transducer, but, in general, the amplitude of these vibrations of the transducer is quite small, for example, on the order of about 0.001 inches (0.025 mm). With a tool or instrument of the present invention, as shown in FIGS. 2, 3, 4, or 6 installed on the handpiece 100, these vibrations will cause the working tip W of the instrument to reciprocate or move (i.e., vibrate) in a plane generally parallel to the plane of the instrument such that the cutting surface W of the instrument will vibrate (reciprocate) back and forth within this plane and the working or cutting surface W of the instrument will remove tooth material in a highly controllable manner. It will be understood that the amplitude of the cutting surface W of the instrument may be greater than or less than the amplitude of the vibrations imparted into the stud 111 and the amplitude of these vibrations in the tips or instruments will depend in the shape, thickness, diameters, material physical characteristics, modulus of elasticity, transitions and other factors that influence how the tip is rendered resonant and the excursion or amplitude (e.g., the distance moved) by the working surface of the tip when the tip is rendered resonant. Further, the term "ultrasonic" is generally understood to mean the transducer vibrates at a frequency above the threshold of human hearing, typically above 20,000 Hz. However, those skilled in the art will recognize that vibrating handpieces suitable for use with the instruments of this invention may use transducers other than piezoelectric transducers that may vibrate at lower or higher frequencies and as such these lower frequencies are also meant to be included within the term "ultrasonic" even if such frequencies are substantially below 20,000 Hz. and substantially above 40,000 Hz., or frequencies therebetween. One such ultrasonic power supply and handpiece that has been successfully used with the instruments of the present invention is commercially available from Spartan Marketing Group, 1663 Fenton Business Park Court, Fenton, Mo. 63026.

As further shown in FIG. 1, the handpiece 100 may be supplied with water, gas, or other surgical irrigation fluid under pressure from a supply (not shown) via a hose (also not shown) connected to the back of the handpiece. A tube 114 within the handpiece allows the surgical irrigation fluid to communicate with a bore 116 within stud 111 for communication with passageways within the tips or instruments secured to the stud in the manner and for the purposes as will appear. The flow of water or other surgical irrigation fluid to the handpiece may be controlled by operating a foot pedal valve (also not shown) in a manner well known in the art.

Referring now to FIGS. 2–7, a series of instrument or tips, as generally indicated at 10 (FIG. 2), at 30 (FIGS. 3 and 5), at 50 (FIG. 4), and at 70 (FIG. 6) are shown. Each of these tips has a hub H having female threads T therein adapted for threadably receiving the male threads on the output shaft or chuck 111 of handpiece 100 such that vibrations from the transducer 104 are transmitted to the tip and such that the tip will resonate at its natural frequency. Each of the tools or tips 10, 30, 50 and 70 has a shank S leading from the hub to the distal or working end W of the tip with a contra angle C formed in the shank intermediate the hub H and the distal end. More specifically, each of the tips 10, 30, 50 and 70 has a first portion FP of the shank S extending in a generally axial direction with respect to chuck 111 of the handpiece 100 and a tip portion TP extending from the first portion to the working tip W. These tips generally have a bend or contra angle C formed therein between the first portion FP and the tip portion TP of the instrument. The included angle of the contra angle C is the sum of angle M plus angle N, and generally ranges generally between about 90° and about 140°. The preferred values of angles C, M and N are given below for each of the tips 10, 30, 50 and 70. It has been found that contra angles generally within this range result in tips that will readily activate and that allow the clinician to comfortably hold the handpiece and to manipulate the tip while performing the desired procedures.

These tools are preferably constructed of a good medical grade of stainless steel, such as 13Cr-8Mo or 17-4PH stainless steel. However, the tips may also be constructed of a medical grade titanium alloy, such as CP GR 4 or 5, or 6Al4V. These materials are sufficiently hard, durable and flexible to resist breakage under use and have a good fatigue life.

Referring now to FIG. 2, instrument or tip 10 is especially adapted to replace the use of a high speed handpiece bur which has heretofore been used to cut access cavities while performing root canals As indicated at 12, this tip has a tapered surgical length of about 0.40 inches (10.2 mm.), and has a rounded distal end 16 (also referred to as working tip W). The tip has a coated length CL which is coated with a suitable micro-abrasive coating A. A preferred such micro-abrasive coating is a diamond grit coating having a grit size preferably ranging between about 160 and about 260, applied to the coated length 14 of the tip portion TP. It will be recognized by those skilled in the art, however, that the grit size of the abrasive coating may vary widely, depending on the preference of the clinician and the like. Further, other coatings, such as Zirconium oxide over a beaded finished surface and other well known abrasive technologies may be used.

As shown in FIG. 2, the first portion FP of the shank S is angled relative to the hub H at an angle M. This angle M is preferably about 15°, ±3°. Further the tip portion TP of the shank S is angled relative to the first portion of the shank S at an angle N. Preferably, the angle N is about 122°, ±3°. The sum of these angles M+N define the contra angle C to be about 137°±6°. The radius of end 16 is preferably about 0.020±0.003 inches or about 0.51 mm.±0.08 mm. As shown, the tip portion TP of the shank has a distal diameter proximate tip W of about 0.020±0.003 inches, or about 0.51 mm.±0.08 mm. The diameter of the tip portion at the end of the coated length CL is about 0.040±0.003 inches (about 1.02 mm.±0.08 mm). By way of example, the tip portion TP may have a constant taper increasing from a tip diameter of about 0.020 inches to about 0.040 inches (0.51 mm. to about 1.02 mm.) over a length of about 0.40 inches (10 mm.), and this constant taper extends along the full length of the shank S from tip W to hub H. However, those skilled in the art that other dimensions may be employed for such a tip.

The above-noted diameter of tip W and the resultant narrowness of the tip portion TP of tip 10 promotes visibility to the clinician as the access within the tooth is made, particularly when the working tip W is deep in the canal. In addition, the contra angle C and the size of tip 10 replicates the size, shape and angles of the high speed handpiece and bur which it replaces so that the instrument "feels" familiar to the clinician. With the provision of the fine grit abrasive coating A (as hereinafter specified) applied to the surgical length 14 and to the end 16 of the tip 10, and with the above-specified radius for working tip W, tip 10 allows the clinician to readily perform cutting procedures and to refine the access line angles so that they drop smoothly into canal orifices without the irregular cutting of the prior art sharp tipped ultrasonic instruments which were heretofore used. The smooth extensions of the access line angles dropping smoothly into each canal orifice that can be readily achieved with tip 10 of the present invention allows files and obturation materials to be quickly and easily dropped into the canals without bringing a mirror into the field of view which blocks the visibility to the clinician. Importantly, the shape of tip 10 allows the refinement of the access line angle thus creating the form required for safe rotary instrumentation.

Tip 10 is particularly useful for gross dentin removal, moving access line angles, cutting a groove in the mesial access wall to drop into MB2 canals, and for quickly un-roofing pulp chambers. Because of the radiused tip geometry of tip 10, entry into each canal orifice is facilitated as is the creation of smoothly troughed surfaces needed to find reclusive MB2 canals.

Further as shown in FIG. 2, tip 10 has a water or irrigation fluid port 18 positioned in hub H for ejecting a stream of fluid (e.g., water or other surgical irrigation fluid and may be include irrigation gases) from the port toward the working end 16 of the tip in the plane of the tip thereby to irrigate the operating site and to carry away debris and the like. While those skilled in the art will recognize that the diameter of port 18 may vary widely, depending on the application, it has been found that a port diameter of about 0.084 inches (2.2 mm.) has worked satisfactorily. Port 18 is supplied with the irrigation fluid under pressure through a channel 20 in hub H. The irrigation fluid is supplied to the handpiece 100 from a supply (not shown) via tube 114 in the handpiece which in turn supplies the fluid under pressure to the bore 116 in the output stud 111 of the handpiece. As previously noted, a foot operated valve (not shown) may be used to initiate and stop operating of the ultrasonic handpiece. A valve on the control panel of the handpiece may be used to control the flow of the irrigation fluid through the handpiece and through irrigation fluid port 18 in the conventional manner well known to those skilled in the art.

Figure 5:
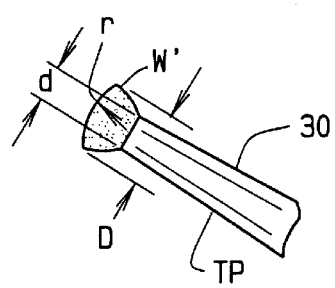
FIG. 5 is an enlarged view taken along line 5—5 of the distal end portion of the tip shown in FIG. 3.

Referring now to the tip 30 illustrated in FIGS. 3 and 5, this tip, like tip 10 described above, has a hub H, a contra angle C and a working end or distal tip W. However, the angle M' of tip 30 is shown to be about 17°, ±3°, the angle N' is shown to be about 121°, ±3° such that the contra angle C for tip 30 is about 138°, ±6°. The length L of the shank from contra angle C to the working tip W' is about 0.68 inches±0.005 inches (17.25 mm.±0.125 mm.). As shown in FIGS. 3 and 5, tip 30 has an enlarged or bulbous working tip W' at its distal end. This enlarged working tip W' has a diameter D (see FIG. 5) perpendicular to the axis of the tip of about 0.54±0.003 inches (13.7 mm.±0.07 mm.). The diameter d of the tip portion TP contiguous the working tip W' is substantially smaller than the diameter of tip W'. In accordance with this invention, tip W' may range from about 1½ to about four times larger in cross sectional area than the contiguous tip portion, but preferably it ranges from about 1½ to about 2 times larger than the cross sectional area of the proximate portion of the tip portion TP.

As best shown in FIG. 5, the outer end face of this enlarged tip is part spherical in shape having a radius r of about 0.061±0.008 inches (1.55 mm.±0.2 mm.). As shown, the diameter of the most distal end of shank S where it is jointed to tip W' is about 0.030 inches and the distal end of the tip 30 smoothly tapers outwardly for a diameter of about 0.030 inches to a diameter of about 0.084±0.002 inches proximate hub H. In accordance with this invention, the part spherical end face of working tip W' is coated with a suitable micro-abrasive coating. Preferably, this abrasive coating is a diamond grit ranging between about 160–230 grit size, and more preferably between about 200–230 grit size, but those skilled in the art will recognize that a wide variety of grit sizes may be used with all embodiments of the instruments described herein. It will be appreciated that such abrasive may be used on all of the tips 10, 30, 50 and 70. In regard to tip 30, this coating is preferably applied only to the outer end face of the bulbous working tip W', but, it may also be applied to the sides of the tip W' and to part of the tip portion TP of the shank proximate the working tip W'. Further, tip 30 has a irrigation fluid port 18 in its hub H similar to tip 10 heretofore described.

Referring now to tip 50 shown in FIG. 4, this tip is similar to tips 10 and 30 heretofore described. More specifically, tip 50 has an angle N'' of about 116°±3°, and an angle M'' of about 13°±3°. Thus, the included angle constituting contra angle C for tip 50 is about 129°±6°. In addition, the offset O of the contra angle C is about 0.168±0.01 inches (4.27±0.25 mm). As shown in FIG. 4, an irrigation fluid outlet port 18'' is provided in the bottom of tip portion TP of shank S, and is preferably located in close proximity to working tip W'' so as to eject a stream of water or other surgical irrigation fluid directly onto the operating site so as to flush debris from the site and onto the working tip W'' so as to cool the working tip. It will be noted that the fluid channel 20'' extends generally axially through hub H and shank S of tip 50 to port 18''. This fluid channel and fluid port are preferably formed within the tip by an electro-discharge machining (EDM) process, as is well known in the art.

In use, the irrigation fluid travels substantially the length of the tip 50 and effects cooling of the tip over the full length of the tip. As the water or irrigation fluid is ejected from port 18'', it is sprayed onto the most distal portion of the shank between the port and the working tip W'' so as to cool this outermost portion of the tip. Preferably, the water port is located in the bottom of the shank so that the fluid ejected from the port is generally within the plane of the tip 50. The distal end of tip 50 is preferably coated with a micro-abrasive coating, such as the diamond grit coating as heretofore describe, and has a coated length CL'' of about 0.25 inches (6.35 mm.). The diameter or working tip W'' is preferably about 0.019±0.002 inches (0.48 mm.±0.05 mm.). Tip 50 has a diameter proximate tip W'' of about 0.020 inches (0.5 mm.) to a diameter proximate hub H of about 0.084 inches with a constant taper therebetween.

Figure 6:
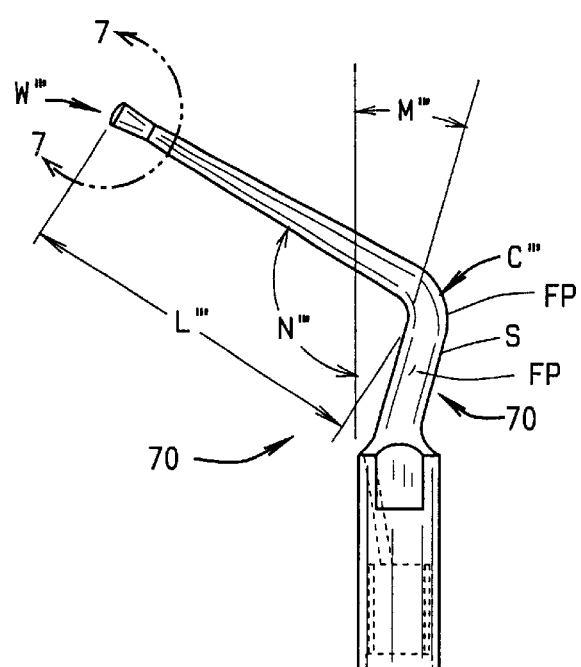
FIG. 6 is an elevational view of still another embodiment of the tip or instrument of the present invention having an enlarged working end with a radiused outer or distal end face constituting the operating surface of the instrument and having a micro-abrasive coating applied thereto.
Figure 7:
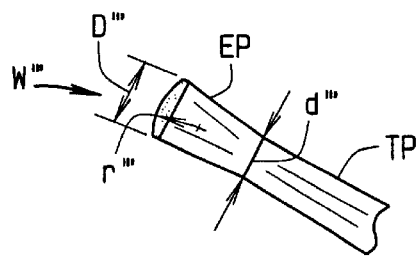
FIG. 7 is an enlarged view taken along line 7—7 of FIG. 6 illustrating the radiused outer end of the instrument shown in FIG. 6.

Referring now to the tip 70 illustrated in FIGS. 6 and 7, this tip also has a hub H, a contra angle C and a working end or distal tip W. However, the angle M''' of tip 30 is shown to be about 17°, ±3°, the angle N''' is shown to be about 121°, ±3° such that the contra angle C''' for tip 30 is about 138°, ±6°. The length L''' of the shank from contra angle C''' to the working tip W'''is about 0.68 inches±0.005 inches (17.25 mm.±0.125 mm.). Tip 70 has an enlarged or bulbous working tip W''' at its distal end. This enlarged working tip W''' preferably has an outer diameter D''' (see FIG. 7) perpendicular to the axis of the tip ranging between about 0.0362±0.001 inches (0.93 mm.±0.07 mm.) and about 0.050±0.003 inches (1.29 mm.±0.07 mm.). The working tip W''' has an end portion EP which is joined to the distal end of tip portion TP. As shown in FIGS. 5 and 7, the end portion EP has a reverse taper (i.e., it is smaller in diameter at its proximal end than at its distal end) and has an inner diameter d''' ranging between about 0.033 inches±0.003 inches (0.87 mm.±0.07 mm.) and about 0.030 inches±0.003 inches (0.77±0.07 mm.) resulting in a "necked down" intersection between end portion EP and tip portion TP. As a result, the diameter of tip portion TP adjacent the working tip W''' is smaller than the diameter of tip W' of the embodiment shown in FIG. 5. The length of the end portion EP is preferably about 0.071 inches (1.82 mm.), but it may vary considerably therefrom (e.g., ±50%). Tip W''' may range from about unity to about four times larger than diameter d''', but, preferably, it ranges from about 1.05 to about 2 times larger. The end face of working tip W' has a part-spherical radius of about 0.061 Inches (1.57 mm.), but those skilled in the art will recognize that the radius of the end face can vary considerably (e.g., ±50%). In addition, the radiused end face of tip W''' has a micro-abrasive material applied thereto so as to constitute the working surface of the tip. It will be appreciated that if the ratio of the outer end of the end portion EP to its inner end is close to the minimum, as stated above, the less reversed tapered geometry of the end portion presents a non-cutting surface to the access wall thus helping to insure that cuffing of the tooth material only occurs on the pulp chamber floor. It has been found that the reverse taper of the end portion EP and the necked down transition to the regular tapered tip portion TP enhances the ultrasonic activation of the tool in that it appears that more power (amplitude) is made available at the working surface of the tip. Of course, the micro-abrasive abrasive may be a diamond or other coating as described above, and it may optionally be applied to areas other than merely to the end face of the working tip. If a diamond coating is used as the abrasive, a 200–230 grit diamond coating may be preferred.

However, depending on the application, other grit sizes will work well.

In operation, with handpiece 100 energized by its ultrasonic power supply (not shown) at ultrasonic frequencies, the chuck 111 of the handpiece is vibrated generally in axial direction. This in turn imparts ultrasonic vibrations into the hub H of any of the tips 10, 30, 50, or 70 threaded on (or otherwise operatively coupled to) the handpiece. This causes the tip to activate (i.e., to resonate) at its natural frequency which in turn causes the tip to vibrate generally in the plane of the tip such that the tip portion TP serves as a cantilevered vibrating arm which in turn causes the working tips W, W', W" or W'" to vibrate in an arc having a radius approximately of the cantilevered end of the tip portion TP. The amplitude of the vibration of the working tips W, W', W" or W'" of the tips 10, 30, 50, or 70 will vary depending on the geometry of the tip and the power supplied by the handpiece 100, but generally the working tip will experience excursions ranging between about 0.001 inches and 0.005 inches (0.025 mm. and 0.125 mm.). The use of the various tips has been described above.

In view of the above, it will be seen that the several objects and features of this invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A dental instrument for use on an ultrasonic dental handpiece for performing endodontic procedures, said handpiece having an ultrasonic transducer therein and an output chuck operatively coupled to said transducer such that when the transducer is rendered resonant, said instrument having a hub adapted to be operatively coupled to said output chuck and a shank portion extending from said hub, a first portion of said shank portion extending in a generally axial direction from said hub and tip portion extending from said first portion, said shank portion having a bend therein between said first portion and said tip portion ranging between about 90° and about 140°, said tip portion having an enlarged free end portion having a substantially conical body and an end face, said conical body having a proximal end joined to said tip portion, said end face having a cross sectional diameter of about one-and-one-half times or more than the diameter of said tip portion proximate said end portion, said end face having a part spherical surface having a spherical radius from about one times to about three times the diameter of said tip portion at the intersection of said tip portion and said end portion, said end face having an abrasive coating thereon so that upon activation of said instrument by said transducer, said tip portion and said end portion vibrates in a plane including said shank portion and tip portions.

2. A dental instrument as set forth in claim 1 wherein upon operatively coupling said hub to said output chuck and upon energization of said transducer, said instrument is activated such that said instrument vibrates in said plane including said shank portion and said tip portion of said instrument such that said end face of said tip portion has an amplitude ranging between about 0.025 mm and about 0.125 mm.

3. A dental instrument as set forth in claim 1 wherein said abrasive coating applied to said end face is a micro-abrasive coating applied thereto having a grit size ranging between about 160 and 260.

4. A dental instrument as set forth in claim 3 wherein said micro-abrasive coating is a diamond coating.

5. A dental instrument as set forth in claim 1 wherein said end face has a spherical end having a radius of about 0.0600 inches plus or minus 50%.

6. A dental instrument as set forth in claim 1 wherein said abrasive coating is applied only to the end face of said end portion.

7. A dental instrument for use on an ultrasonic dental handpiece for performing endodontic procedures, said handpiece having an ultrasonic transducer therein and an output chuck operatively coupled to said transducer such that when the transducer is rendered resonant, said instrument having a hub adapted to be operatively coupled to said output chucks, a shank portion extending from said hub, and a tip portion extending from said shank portion, said shank portion extending in a generally axial direction from said hub having a bend therein between said hub and said tip portion ranging between about 90° and about 140°, said tip portion having an end portion with the outermost end of said end portion constituting a working surface having a suitable abrasive coating applied thereto, said end portion and said tip portion each being of circular cross section, said end portion being tapered and having an inner end where the diameter of said outermost end ranges between about 1.1 to about 1.5 times or more greater than the diameter of said inner end, said tip portion being tapered along its length with the diameter of the proximate end of said tip portion being larger than the diameter of the distal end of said tip portion, with the diameter of said distal end of said tip portion being substantially equal to the diameter of the inner end of said end portion.

8. A dental instrument as set forth in claim 7 wherein said outermost end of said end portion is part spherical and wherein said abrasive coating is applied only thereto.

* * * * *